United States Patent
He et al.

(10) Patent No.: US 12,016,634 B2
(45) Date of Patent: Jun. 25, 2024

(54) METHODS AND APPARATUS FOR ELECTROMAGNETIC SOURCE IMAGING USING DEEP NEURAL NETWORKS

(71) Applicant: CARNEGIE MELLON UNIVERSITY, Pittsburgh, PA (US)

(72) Inventors: Bin He, Pittsburgh, PA (US); Rui Sun, Pittsburgh, PA (US); Abbas Sohrabpour, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 485 days.

(21) Appl. No.: 17/315,691

(22) Filed: May 10, 2021

(65) Prior Publication Data
US 2021/0346096 A1 Nov. 11, 2021

Related U.S. Application Data

(60) Provisional application No. 63/022,876, filed on May 11, 2020.

(51) Int. Cl.
| | |
|---|---|
| A61B 34/10 | (2016.01) |
| A61B 5/245 | (2021.01) |
| A61B 5/369 | (2021.01) |
| G06F 30/23 | (2020.01) |
| G06N 3/08 | (2023.01) |

(52) U.S. Cl.
CPC .............. *A61B 34/10* (2016.02); *A61B 5/245* (2021.01); *A61B 5/369* (2021.01); *G06F 30/23* (2020.01); *G06N 3/08* (2013.01); *A61B 2034/105* (2016.02)

(58) Field of Classification Search
CPC ......... A61B 34/10; A61B 5/245; A61B 5/369; A61B 2034/105; A61B 5/378; A61B 5/383; A61B 5/725; A61B 5/7267; A61B 5/246; G06F 30/23; G06N 3/08; G06N 3/044; G06N 3/045
See application file for complete search history.

(56) References Cited

U.S. PATENT DOCUMENTS 9,116,835 B1 * 8/2015 Smyth ................... A61B 5/369

OTHER PUBLICATIONS

Cui et al. 2019 China Communications Jul. 2019: 131-143 (Year: 2019).*
He et al. 2018 Annu. Rev. Biomed. Eng. 20:171-96 (Year: 2018).*

(Continued)

*Primary Examiner* — Keith M Raymond
*Assistant Examiner* — Patrick M Mehl
(74) *Attorney, Agent, or Firm* — KDW Firm PLLC

(57) ABSTRACT

Disclosed herein are methods and apparatus for the imaging of brain electrical activity from electromagnetic measurements, using deep learning neural networks where a simulation process is designed to model realistic brain activation and electromagnetic signals to train generalizable neural networks and a residual convolutional neural network and/or a recurrent neural network is trained using the simulated data, capable of estimating source distributions from electromagnetic measurements, and their temporal dynamics over time, for pathological signals in diseased brains, such as interictal activity and ictal signals, and physiological brain signals such as evoked brain responses and spontaneous brain activity.

25 Claims, 16 Drawing Sheets

(56) References Cited

OTHER PUBLICATIONS

Wei et al. 2020 NeuroImage 211: article 116595 16 pages; online ePub Dat. Feb. 3, 2020 (Year: 2020).*
Kunze et al. 2016 NeuroImage 140:174-187 (Year: 2016).*
Cabrerizo et al. 2011 IEEE Signal Processing in Medicine and Biology Symposium SPMB 2011 1-6 (Year: 2011).*
Leistritz et al. 2016 Proc IEEE 104:262-281 (Year: 2016).*

* cited by examiner

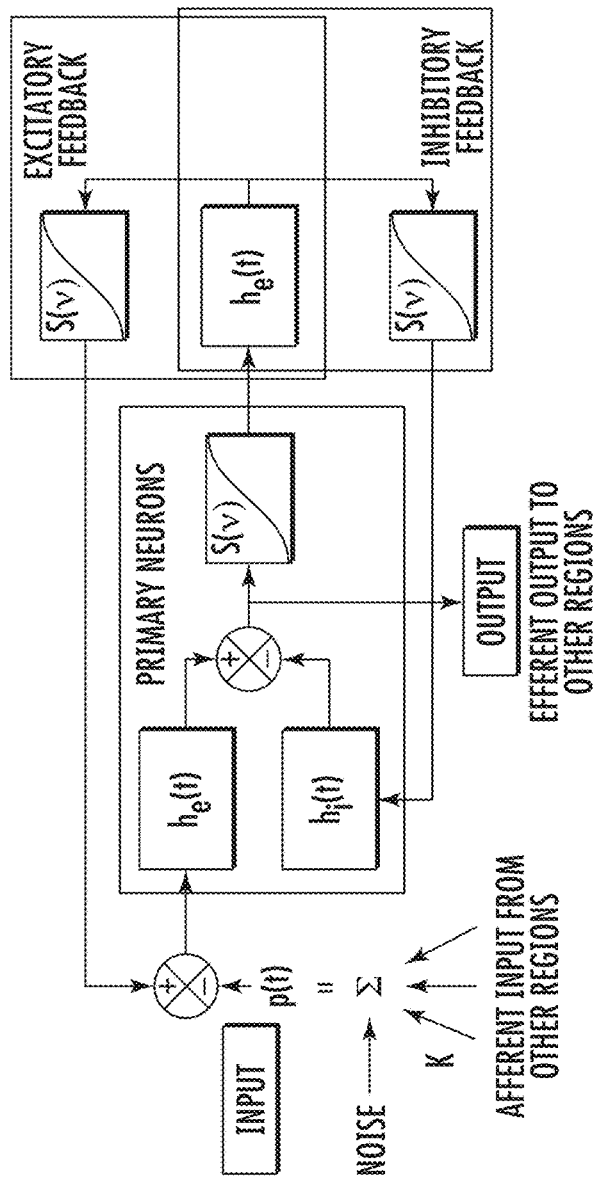

FIG. 4A

| EQUATION | INTERPRETATION | PARAMETER | DEFINITION | VALUE |
|---|---|---|---|---|
| $S(v) = \dfrac{2e_0}{1+e^{r(v_0-v)}}$ | TRANSFORMING THE AVERAGE MEMBRANE POTENTIAL TO AN AVERAGE PULSE DENSITY | $2e_0$ | MAXIMUM FIRING RATE | $2.5\ s^{-1}$ |
|  |  | $v_0$ | PSP AT $e_0$ | 6 mV |
|  |  | r | STEEPNESS OF THE SIGMOID | 0.56 mV |
| $h_e(t)$ $= u(t) \cdot Aate^{-at}$ | IMPULSE RESPONSE IN EXCITATORY/INHIBITORY CASE | A<br>B | AVERAGE EXCITATORY/INHIBITORY SYNAPTIC GRAIN | 3.25 mV<br>22 mV |
| $h_i(t)$ $= u(t) \cdot Bbte^{-bt}$ |  | a<br>b | AVERAGE MEMBRANE TIME CONSTANT & DENDRITIC TREE TIME DELAY | $100\ s^{-1}$<br>$50\ s^{-1}$ |

FIG. 4B

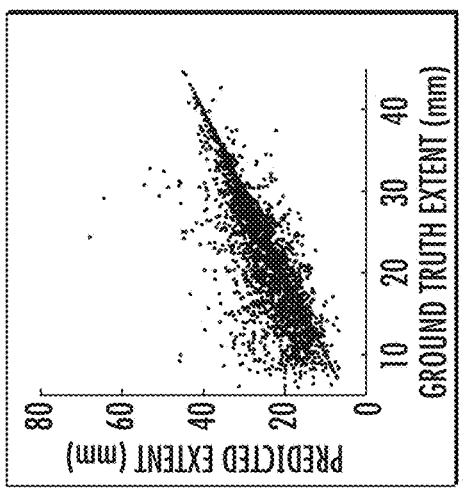
FIG. 9A
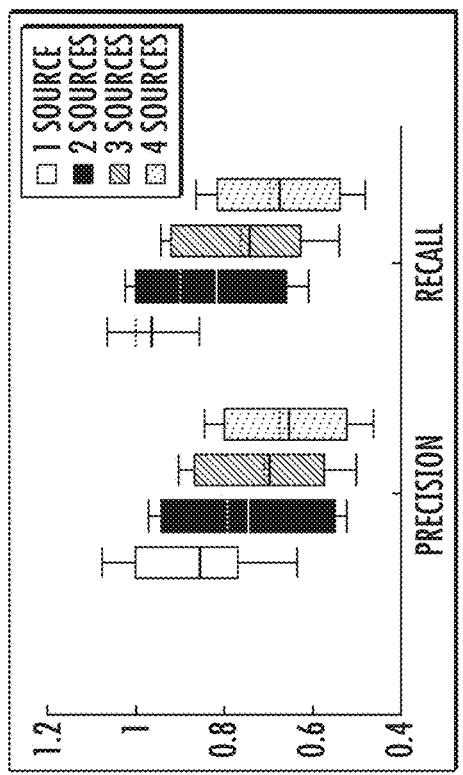
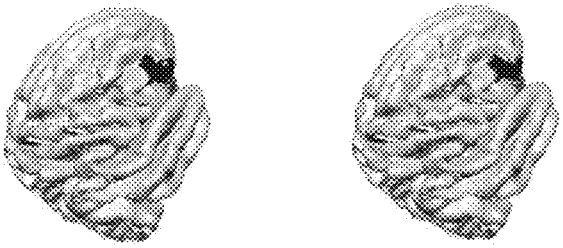
FIG. 9B
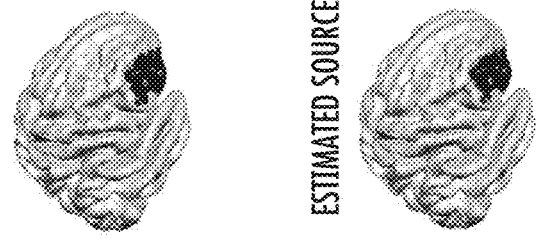
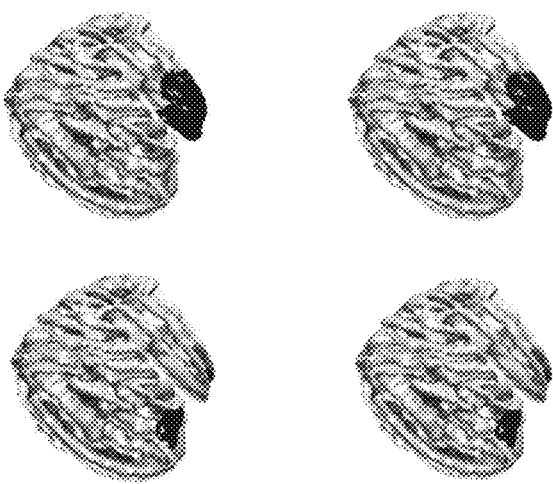
FIG. 9C

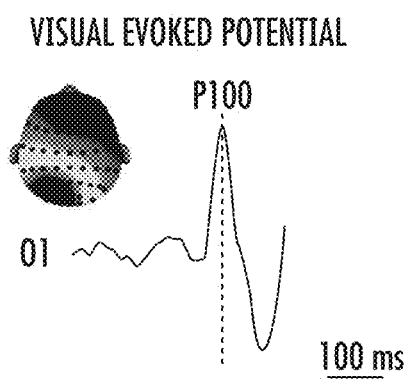
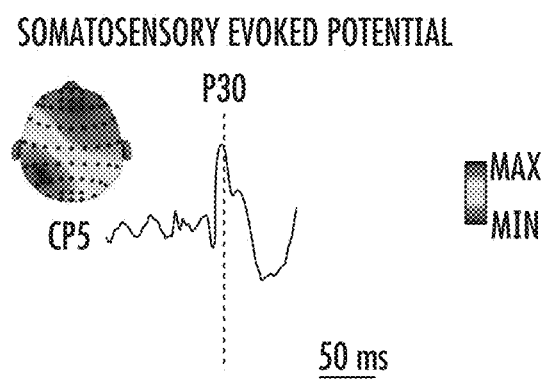
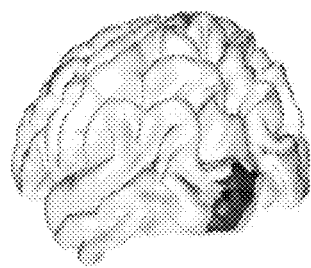
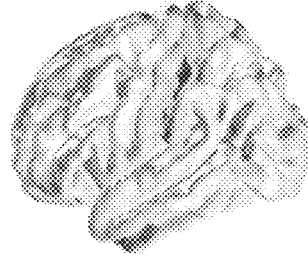
FIG. 14A
FIG. 14B

METHODS AND APPARATUS FOR ELECTROMAGNETIC SOURCE IMAGING USING DEEP NEURAL NETWORKS

RELATED APPLICATIONS

This application claims the benefit of U.S. Provisional Patent Application No. 63/022,876, filed May 11, 2020, the contents of which are incorporated herein in their entirety.

GOVERNMENT INTEREST

This invention was made with government support under grants from the National Institutes of Health, Nos. EB021027, NS096761, EB029354, MH114233 and AT009263. The government has certain rights in this invention.

BACKGROUND

Electroencephalography (EEG) and magnetoencephalography (MEG) are noninvasive techniques that measure synchronized activities of neuronal ensembles in the brain. Scalp EEG/MEG topography provides spatial information about the underlying brain electrical activity. However, scalp topographical maps can only provide a rough estimation of the underlying sources due to the volume conduction effect. Electrophysiological source imaging (ESI) was developed to significantly enhance the spatial resolution of noninvasive EEG/MEG. ESI is the process of estimating the underlying brain electrical activity from EEG (or MEG) traces, through a deconvolution process, to find the brain source distributions that fit the recorded EEG (or MEG). However, it is challenging to localize and image the brain electrical activity precisely and reliably with only a few hundred sensors, because of the ill-posed nature of the inverse problem, as different source distributions can produce similar potentials/fields at the scalp.

To overcome the challenges posed by the limited number of measurements and the volume conduction effect, current ESI methods require a priori assumptions to regularize the inverse problem and to ultimately find a unique solution. The dipole source localization methods need to know the number of sources a priori, and when that information is not available, distributed-source models can be used with regularization priors to restrict the solution space. Regularization terms could be based on imposing constraints on the energy, covariance, sparsity level or multiple different constraints on the solution.

These methods require parameter tuning to balance between fitting the recorded data and satisfying the regularization constraints when solving every instance of a given problem (i.e., for every given EEG/MEG measurement), which could be a time-consuming process.

ESI approaches based on deep learning attempt to capture the correct mapping between signals and source spaces through a large amount of training data which is ultimately represented by the weights and non-linear units in its layers. Another feature of the deep learning approach is that, after the time-consuming training process, the algorithm is quite efficient and fast when applied to new data. This eliminates the need to search for hyperparameters for each new instance of EEG/MEG measurements, thereby providing an opportunity for real-time source imaging.

To develop a successful analysis tool using deep learning, the neural network needs to be successfully trained. For model training, it is crucial to obtain enough labeled data to provide a proper mapping pattern from input to output. Because the amount of EEG/MEG data with source distributions correctly labeled is usually limited, computational models can be used to generate the training data, as well as the testing data, to quantitatively evaluate the model performance.

There are biophysical models that take the neuronal dynamics based on cellular modeling and the interaction between different brain regions into account, and the source activities of the whole brain are generated from these interactions. One well-studied model is the neural mass model (NMM) which is based on neurophysiological principles. A NMM models the average electrical activity of principal neurons and interneuron ensembles of a cortical region. The temporal behavior of the model is defined by differential equations and model parameters, such as tissue properties (e.g., excitability, and inter-regional connectivity). These models run on noise and, once a few parameters are set, they can autonomously generate EEG-like (or MEG-like) activity. NMM has been used in conjunction with the forward modeling of electromagnetic field propagation in the head tissue (i.e., EEG and MEG lead-field), to provide more insight into the underlying pathophysiological mechanisms of epileptic activity.

SUMMARY OF THE INVENTION

The present invention integrates a deep learning neural network with realistic dynamic brain models, such as NMM, to provide a framework wherein the forward source-signal relationship can be modeled using neural mass models and a head volume conductor model, and inverse source imaging can be performed by means of a deep learning neural network.

The present invention includes methods for source imaging from electrophysiological recordings (such as EEG or MEG, or even intracranial EEG) that uses dynamically generated data by means of computational models (such as NMM located in a head-brain volume conductor model) to generate synthetic sensor space data which can be used to train a neural network for distributed source imaging. This novel aspect of the invention uses realistic neural mass model-generated data to train a neural network solving the source imaging problem and which is capable of providing distributed source solutions.

The invention has applicability in various applications, including imaging and localizing epilepsy sources and imaging physiological or various pathophysiological sources associated with brain function or dysfunction. When the neural network is trained with realistic simulation brain activities generated by interconnected NMMs, it can outperform conventional ESI methods. The invention provides superior performance generalized to different types of signals.

The present invention also includes an apparatus comprising a recording component for measuring EEG or MEG signals at a plurality of sensors, a pre-processing unit for pre-processing EEG or MEG data, an imaging unit where a deep learning neural network is trained using simulated labeled data that is generated by realistic neuronal computational models such as NMM, and a display unit which displays source imaging results together with anatomic information of the brain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A is a schematic showing the structure of a single-element Jansen-Rit model.

FIG. 4B shows the equations and standard values for the parameters of the model of FIG. 4A.

FIGS. 9A-9C show example results for the present invention for estimating the extent of simulated sources in various portions of the brain.

FIGS. 14A-14B show example results for the present invention to image cortical activity of visual evoked potentials in a healthy human subject in FIG. 14A, and somatosensory evoked potentials in a healthy human subject in FIG. 14B.

DETAILED DESCRIPTION

While the present invention can be applied to EEG, MEG and even intracranial EEG data, for simplicity, the invention will be explained in the context of its application to EEG data. Examples of applying the invention on multiple types of scalp data, i.e. EEG/MEG, will be shown. The invention addresses the fundamental problems for training a deep neural network to image and localize brain electrical activity. The invention first addresses the challenge of generating enough training data that resembles real EEG data. Because an actual mapping of source signals to an EEG trace would require invasive probing of the brain of a subject, a suitable quantity of data for training a deep neural network is unavailable. Additionally, the invention addresses the robustness of a model trained on these source models in comparison to variations in the input data. Finally, the invention addresses how well a model trained in accordance with the present invention performs, given real EEG or MEG recordings.

Figure 1:
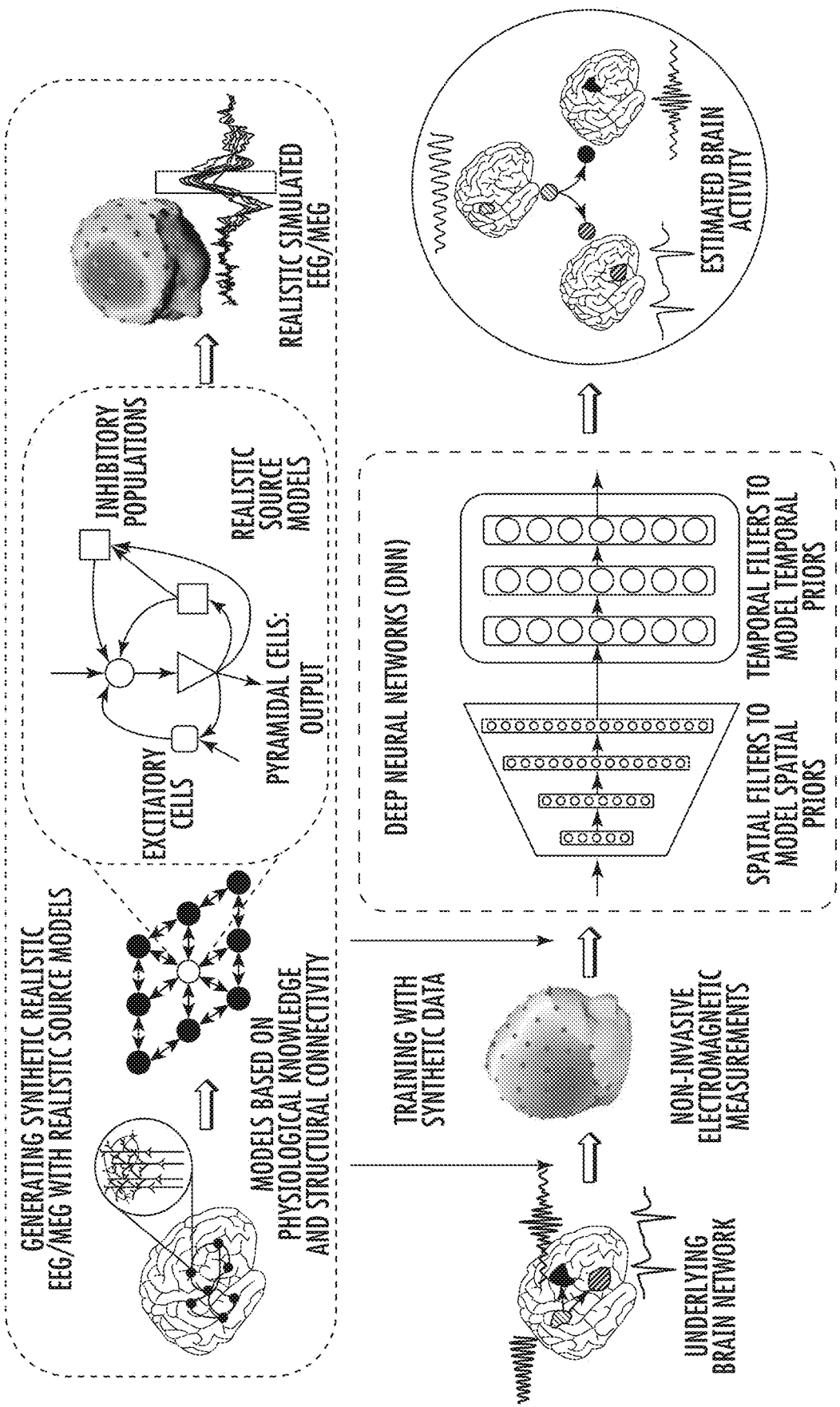
FIG. 1 is a schematic illustration of the methods for EEG/MEG source imaging using deep learning neural networks.

As illustrated in FIG. 1, signals generated by a realistic source model are used as the underlying brain activity to generate the synthetic noninvasive EEG or MEG signals. The synthetic scalp and the corresponding brain signals are used as input to train a neural network which, in various embodiments of the invention, may be a deep neural network (DNN). With proper training, the neural network returns source distributions corresponding to an EEG or MEG input that represent spatio-temporal distributions of brain activity and functional networks.

Figure 2B:
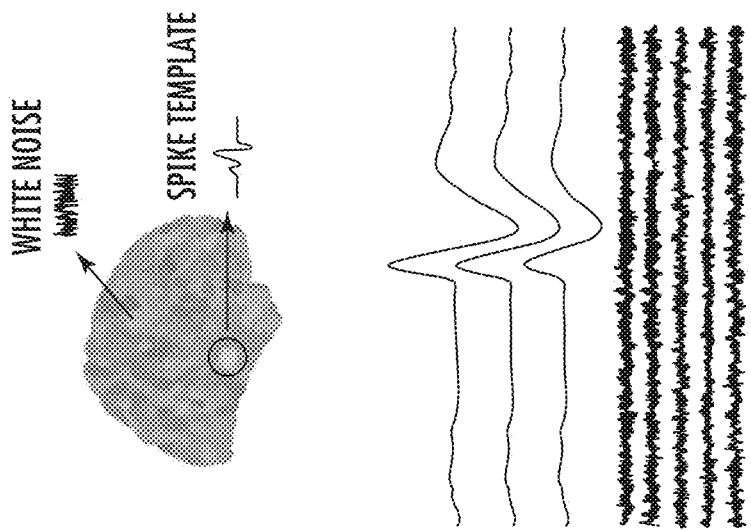
FIGS. 2A-2B show two example embodiments of source models, and sample signals generated by the two models.
Figure 2A:
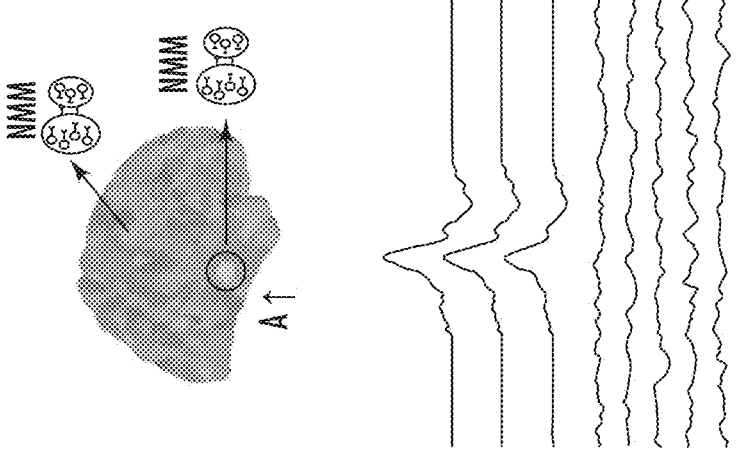

Example illustrations of realistic source models in the present invention are provided in FIGS. 2A-2B. In this example embodiment, brain is divided into a number of regions and regional brain electrical activity is modeled using a neural mass model (NMM), as shown in FIG. 2A, or a template source model, as shown in FIG. 2B. In the example template source model, regional neural activity is represented by a current density distribution determined by the physical property of regional sources, where template source profiles can be a pre-defined source waveform or recorded electrophysiological signals inside the brain such as intracranial EEG recordings in patients undergoing intracranial monitoring. In the NMM model, regional brain activity is represented by a biophysically inspired NMM model reflecting the cellular and cell network activity of neural tissues.

Figure 3:
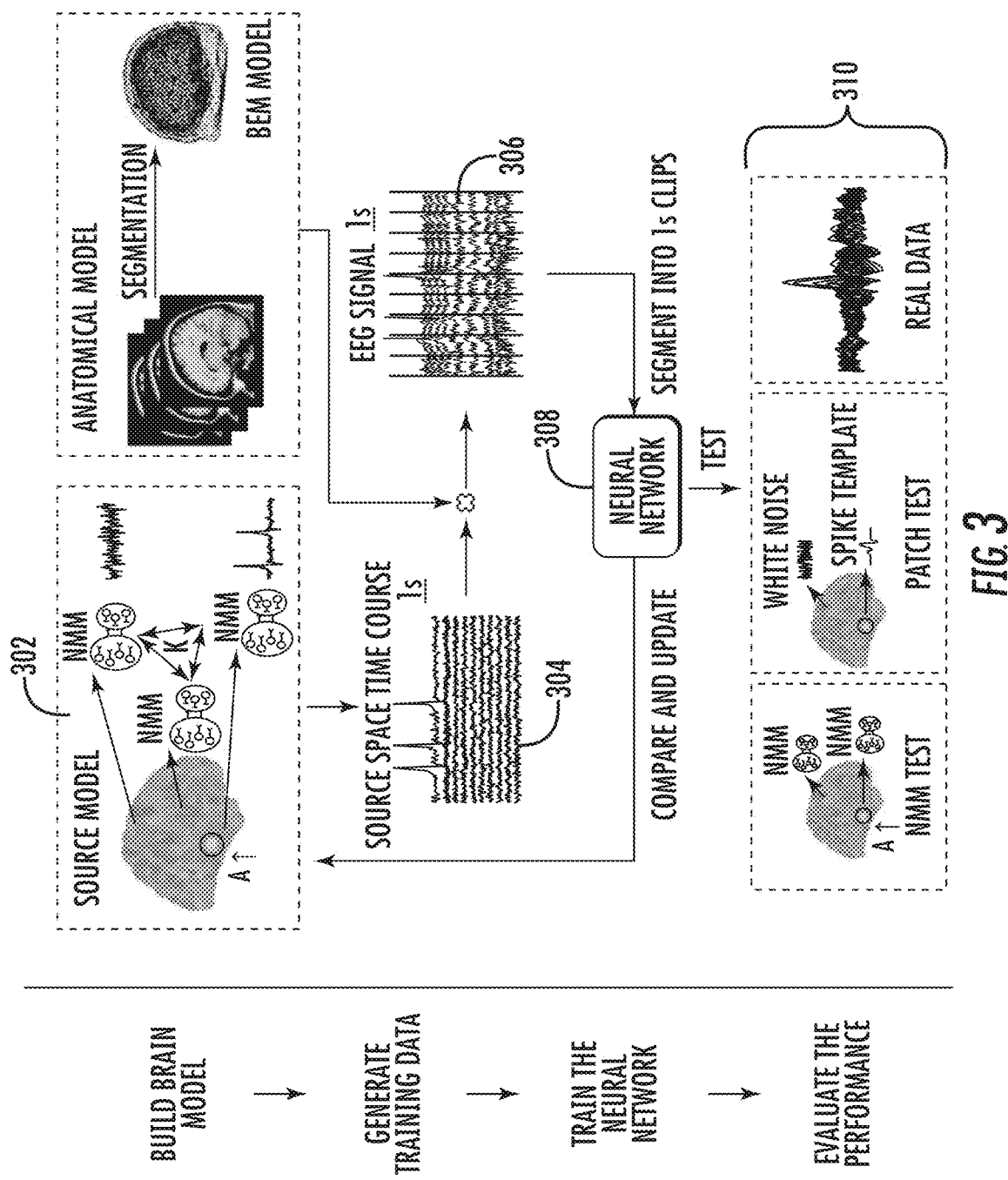
FIG. 3 is a graphical representation of an example embodiment for EEG source imaging using neural network.

An example embodiment of the present invention is illustrated in FIG. 3, where NMMs 302 were used as the realistic source model. Simulated source signals 304 generated by NNM 302 were used as the underlying brain activities and the simulated scalp EEG signals 306 were obtained by multiplying the generated NMM source signals by a lead-field matrix. The synthetic scalp EEG signals were used as input to train a neural network 308. The neural network 308 was updated iteratively to learn the mapping relationship between the brain source signals and scalp EEG signals. Lastly, three sets of data 310 with different source signal distributions were tested on the trained network.

While the NMM models were used in the example embodiment illustrated in FIG. 3, the template source model, shown in FIG. 2B, where the realistic brain sources are simulated using distributed physical source models such as current density distribution, can also be used to simulate brain electrical activity, generate scalp EEG signals, and train a neural network as shown in FIG. 3.

Source Signal Simulation—

The temporal dynamic of the brain activity can be generated using interconnected neural populations, each represented by a physiologically relevant model. The Jansen-Rit model, shown in FIGS. 4A-4B, is a reasonable model for generating brain electrical activity, including evoked responses, interictal spike activities as well as spontaneous brain activity such as ictal activities. The source activity of each brain region is simulated by modeling the interaction of neuron sub-populations through differential equations. The relationship between neuron sub-populations is illustrated in FIG. 4A, while the equations and typical values for the parameters are listed in FIG. 4B.

FIG. 4A shows the structure of a single-element Jansen-Rit model. A single-element Jansen-Rit model simulates three neuron sub-populations: the primary neurons (i.e. pyramidal cells), as well as excitatory and inhibitory interneurons. The influence from other neural populations is modeled as an excitatory input p(t) that represents the average pulse density (i.e., the average firing rate of afferent action potentials). The behavior of each subpopulation is modeled using linear functions $h_e(t)$ and $h_i(t)$ that describe how presynaptic information is transformed into postsynaptic information, and a nonlinear function S(v) that models the change from an average membrane potential of the subpopulation to an average pulse density.

With the typical values provided in FIG. 4B, the NMM network can simulate brain signals similar to resting-state or task state brain activity, and when the average excitatory synaptic gain (defined as A) is increased, it can simulate spike-like activities, which exhibit similarities with interictal spike signals observed in epileptic discharges. Multiple single-element Jansen-Rit models can be connected through a connectivity matrix K, where the input for each single element is the weighted sum of the output of other elements to form a network of interconnected NMMs. By increasing A for one NMM and keeping the other A values the same, the temporal dynamic of the brain with one "hyperexcitable" region can be simulated, resembling the simplified dynamics observed in localized brain activation, such as in focal epileptic sources, or evoked brain activation by external stimulation such as visual or somatosensory stimuli.

EEG Signal Simulation—

In one embodiment, a template T1-weighted MRI was used to get the segmentation of the cortical surface, skull and skin. A 64-channel electrode layout was used for the EEG electrode configuration. The lead-field matrix was calculated with the conductivity values of 0.33, 0.0165 and 0.33 S/m for the brain, skull and scalp, respectively, using the boundary element method (BEM) model. Other numerical techniques may also be used to derive the lead-field matrix, such as the finite element method and finite difference method, etc. The source space was defined over the cortex by segmenting the whole cortex, in one embodiment, into 994 similarly sized interconnected regions. Current density distribution over the region was summarized into a current dipole for computation, whose time course can be assigned using known neurophysiological activity (such as in the template source model shown in FIG. 2B or generated by the NMM (FIGS. 4A-4B). The connectivity weights K between those regions were calculated from diffusion-weighted MRI images averaged over 5 healthy human subjects.

MEG Signal Simulation—

In another embodiment, a template T1-weighted MRI was used to get the segmentation of the cortical surface, skull and skin. A multi-channel sensor layout was used for the MEG coil configuration. The lead-field matrix was calculated with the conductivity values of 0.33, 0.0165 and 0.33 S/m for the brain, skull and scalp, respectively, using the boundary element method (BEM) model. Other numerical techniques may also be used to derive the lead-field matrix, such as the finite element method and finite difference method, etc. The source space was defined over the cortex by segmenting the whole cortex, in one embodiment, into 994 similarly sized interconnected regions. Current density distribution over the region was summarized into a current dipole for computation, whose time course was generated by the NMM. The connectivity weights K between those regions were calculated from diffusion-weighted MRI images averaged over 5 healthy human subjects.

The brain source signals from all regions were then projected onto the scalp using a lead-field matrix to generate a synthetic, simulated EEG trace. The NMM signal from each region was scaled so that the ratio between the activation signal (such as interictal spike or evoked potential) and the background signal from other regions contributing to the EEG was the same for all simulated data. In other words, cortical regions which had an inherent disadvantage due to their depth were normalized so that they received equal representation in the simulated EEG as regions which had stronger representation. Afterwards, different levels of Gaussian white noise were added to the scalp potential to simulate noise-contaminated EEG measurements, so that the signal-to-noise ratio between the EEG signal and the white noise was 5, 10, 15 or 20 dB, respectively. In one embodiment, the signal was then segmented into 1-second clips and fed as the input into the neural network. In this embodiment, the training data contained about 500,000 extracted spike intervals with different source distributions and noise levels.

In an alternative source modeling method illustrated in FIG. 2B, pre-defined signal templates were used to simulate brain electrical activity. Four different interictal spike signals extracted from EEG recordings of epilepsy patients were used. These extracted signals were assigned to the source region serving as the spike generating cortical region and Gaussian white noise was added to the other regions so as to simulate the effect of the colored noise observed in EEGs from other brain regions, similar to NMM-generated data. After the brain signal was projected onto the scalp, different levels of Gaussian white noise were also added to the simulated EEG. These synthetic data were then used to train a neural network, and brain electrical activity was estimated using the trained neural network.

In one embodiment, the present invention implements a spatiotemporal imaging method using a deep neural network (DNN) for solving the electrophysiological source imaging (ESI) problem from EEG or MEG recordings. The ESI can be formulated mathematically as an optimization problem. For this under-determined optimization problem to be solvable, regularization terms or prior assumptions are necessary. Typically, assumptions about the spatial distribution or characteristics of underlying sources as well as their temporal dynamics need to be made. This naturally translates to solving optimization problems of the following form:

$$\underset{\jmath}{\operatorname{argmin}} \|\phi - \mathcal{K}\jmath\|_p^p + R_s(\jmath) + \mathcal{R}_\mathcal{T}(\jmath) \tag{1}$$

where:
 ϕ is a matrix of EEG (or MEG; or intracranial EEG) recordings over certain time interval;
 $\mathcal{K}$ is the lead-field matrix which models how source current densities (i.e., $\jmath$) are related to the scalp electromagnetic recordings (i.e. ϕ);
 $\mathcal{R}$ is a regularization term that captures spatial priors;
 $\mathcal{R}_\mathcal{T}$ is a regularization term that expresses temporal priors, and p is any real number equal to or larger than 1 (p≥1) which is used to define the p-norm in Eq. (1), such that for vector $x=(x_1, x_2, \ldots, x_n)$, $$\|x\|_p = \left(\sum_{i=1}^{n} |x_i|^p\right)^{\frac{1}{p}}$$

Implementing Eq. (1) in a DNN framework has the advantage that the regularization terms, $\mathcal{R}_S$ and $\mathcal{R}_T$, do not have to be explicitly expressed but instead the DNN structures learn these priors from training examples.

In an embodiment of the present invention to image and localize brain electrical activity from intracranial EEG recordings, the lead-field matrix K in Eq. (1) will be derived by solving Poisson's equation to reflect the relationship between brain sources and intracranial EEG recordings. Other aspects of the invention shall remain similar including realistic source modeling, generating training datasets, training a deep neural network, and estimating brain sources from recorded intracranial EEG signals.

The spatiotemporal EEG data are represented as a matrix of channel cross time. In one embodiment of the invention, a convolutional neural network (CNN) was applied to process the input. A CNN can extract local, common features by using convolution and nonlinear activation functions, and global features can be learned hierarchically by layered computations. Because the activity arising from each source location contributes to all EEG channels, the source activity can be fully estimated if global features are considered and analyzed. To achieve the goal of ESI, which is to estimate underlying brain activities at the source-level, it is important that there are enough convolution filters that have wide-enough receptive fields covering all EEG channels. To aggregate the local spatiotemporal features and unmix the global source information, a neural network of a certain minimum depth is needed.

Figure 5A:
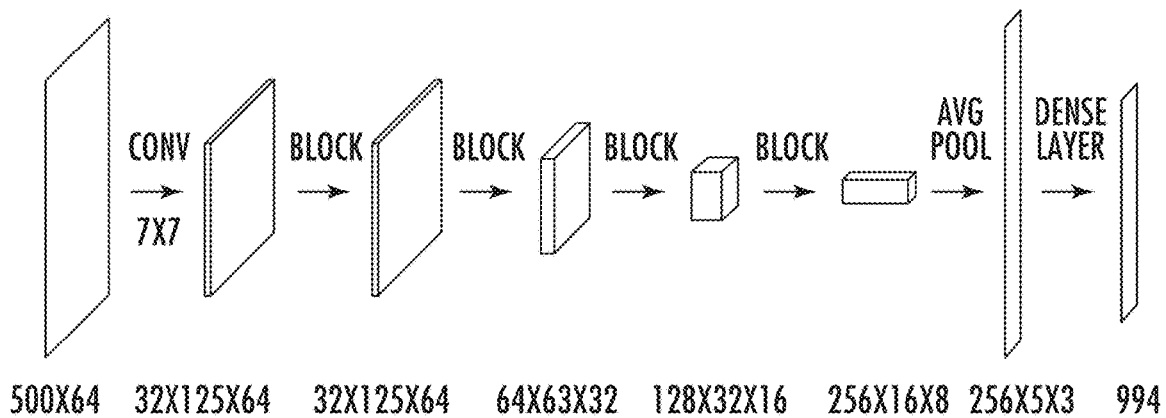
FIG. 5A is a schematic representation of the neural network of a first embodiment of the invention providing only spatial information of the sources.
Figure 5B:
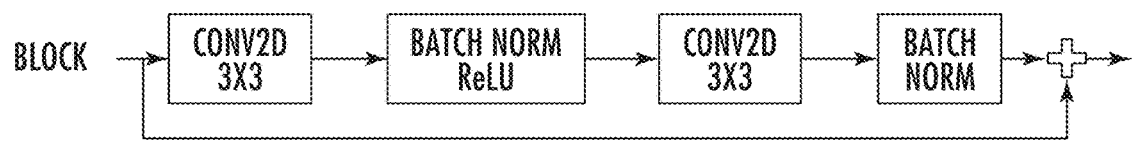
FIG. 5B is a schematic representation of one or more of the blocks shown in FIG. 5A.

In a first embodiment of the invention, the CNN is trained to provide only spatial information of the source. The CNN consists of spatial filters to project scalp potential measurements to source space signals. FIGS. 5A-5B show one possible implementation of the structure of the CNN of the first embodiment. FIG. 5A shows the overall network structures, while FIG. 5B shows the computation inside each residual block.

To mediate the difficulties in training deep neural networks, a residual structure was adopted. Five residual blocks were followed by a pooling layer and a fully connected layer with its output size the same as the number of source regions. Each residual block contained two CNN layers with batch normalization to remove the covariance shift during the training. The original input was added back to the output and fed to the next block through a Rectified Linear Unit (ReLU) activation function. The ESI problem was reformulated as a classification problem and cross entropy between the true source region (i.e., the activation signal generating region) and the predicted source region was used as the loss function. Adam optimizer was used for the training. The whole network was implemented in PyTorch.

In a second embodiment of the invention, the neural network is trained to provide both spatial and temporal information of source. The neural network consists of spatial filters to project scalp potential measurements to source space signals and a temporal filter where current and past values of the time-course of activity from source space signals are used to estimate the source's activity at given time in the output unit. The output of the model is the time-course of activity for every cortical area.

Figure 6:
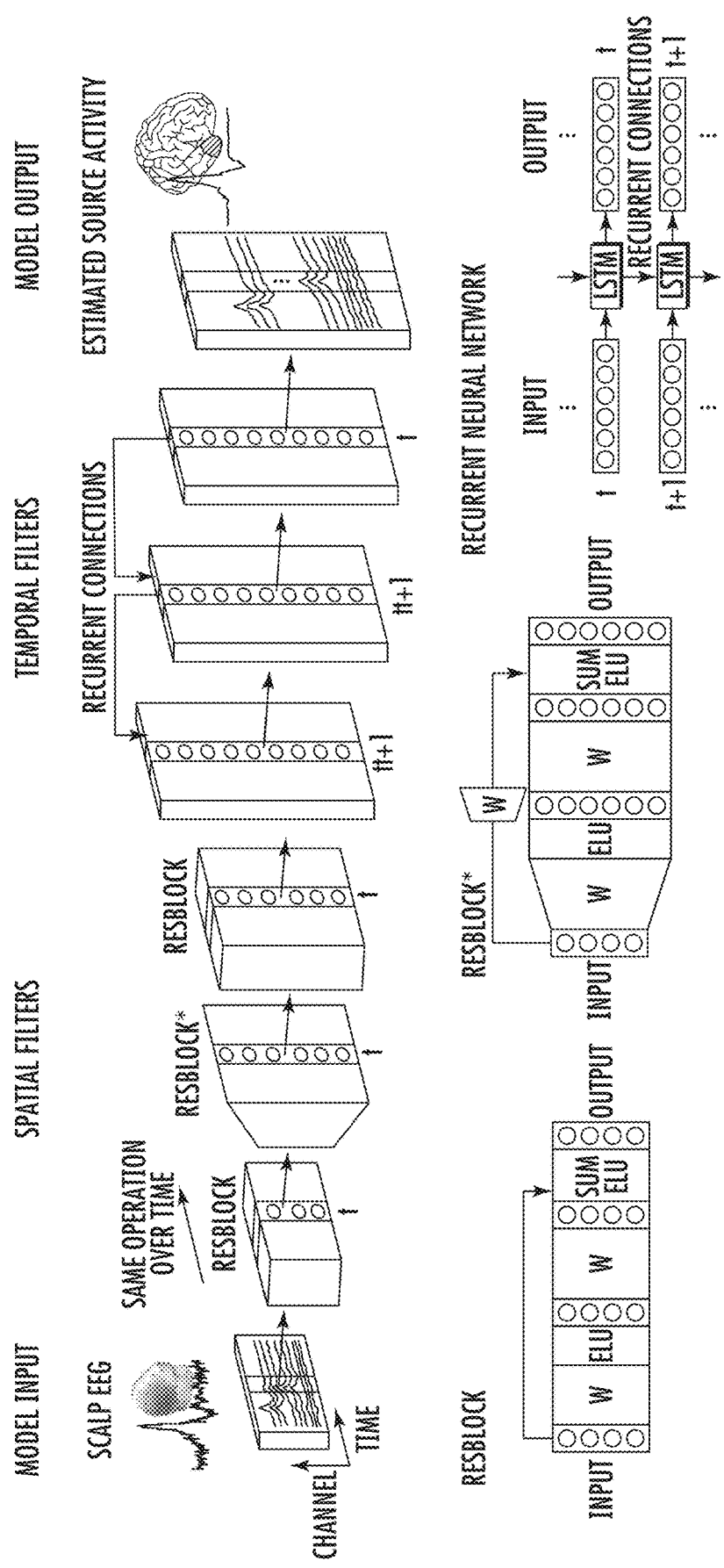
FIG. 6 is a schematic representation of the neural network of a second embodiment of the invention providing both spatial and temporal information of the sources.

FIG. 6 shows the structure of the neural network of the second embodiment. To use previous samples in a time series to better estimate the future values, the neural network employs a recurrent neural network (RNN) for the temporal filtering. RNNs are designed to extract patterns within a string of input. They are typically employed in natural language processing applications to process strings of input characters (i.e., text in foreign language) to strings of output symbols (i.e., text in English). RNNs have proven highly effective in extracting, within a sequence, relationships to model appropriate outputs. In ESI, the input is the time-series from EEG recordings at every time sample, with the goal of estimating the time series of all brain sources in the model. This can be thought of as a multi-variate auto-regressive model. The output of the RNN is fed back into the input layer of RNN (abstractly modeling inter-regional connectivity) and is combined with the instantaneous spatial estimates, $\hat{j}^t$, to integrate model priors with evidence from measurements to ultimately form a final optimal solution, similar to the formula in Eq. (1).

One exemplary implementation of the invention will now be discussed. The exemplary implementation is not meant to limit the scope of the invention in any way but is instead provided as an illustration of practicing the invention.

The current temporal filter has 3 hidden layers and employs Long short-term memory (LSTM) to enable relevant information of previous samples to be used to predict the final output in the temporal filtering process. The spatial filter is composed of 3 blocks of residual architecture (ResBlocks), with gradually increasing dimensions. Training deep networks is challenging due to the gradient vanishing problem and residual structures alleviate this shortcoming extensively. Each ResBlock is composed of two fully connected layers with a skip connection that adding back to the output of the last layer (SUM), and exponential linear unit (ELU) activations are used.

While the example uses of the present invention are illustrated in the implementations with a limited number of layers of the neural networks, the invention is not meant to be limited to a specific range for the number of layers that can be adopted to practice the invention. Such neural network structures may range from a few layers to a very deep network structure, with number of layers of neural network ranging between 3 layers through 300 or more layers.

Extended sources were simulated on the cortex and the corresponding scalp EEG was generated by solving the forward problem. A realistic head volume conductor model consisting of the cortical surface, skull, and scalp was constructed from an MRI of a human subject using the BEM head model with conductivity values of 0.33, 0.0165 and 0.33 S/m for the three layers, respectively. The source space was defined as the grey matter and represented using a 3-dimensional mesh with 20,484 grid vertices with a current dipole at each grid and 40,960 triangular surface elements. The neural field model (NFM) consisted of parcellating the brain into 994 disjoint regions, with each region representing an NMM element capable of generating electrical activity such as inter-ictal spikes or ictal oscillations or evoked activity. Each such region contains 20±13 current dipoles which were oriented perpendicularly to the cortical surface and were assumed to have the same time course generated by the NMM. The connectivity weights K between those regions were calculated from diffusion-weighted MRI images averaged over 5 human subjects. The NFM modeling was conducted by solving a set of differential equations using the stochastic integrator with a step size of 0.5 milliseconds. The data were then downsampled to a sampling rate of 500 Hz.

In one embodiment, a biophysically constrained deep neural network (BioDNN) approach is used to perform the spatiotemporal source imaging, in which brain electrical activity is simulated using biophysical models generating scalp EEG/MEG, and a deep neural network is trained and used for source imaging. The BioDNN can work with multiple activated sources. In one implementation of the invention, the BioDNN model was trained on two-source data where there were two active regions in the source space. Centers from the 994 parcellated brain regions were randomly chosen and a random number of 2-25 regions (from those 994 regions) were grouped as a single source with the same temporal activity to simulate sources with varying extent (ranging from 5 to 45 mm). This compositional source (multiple regions from the 994 parcellations grouped as one source) is referred to herein as a "patch" in the following.

Figure 7A:
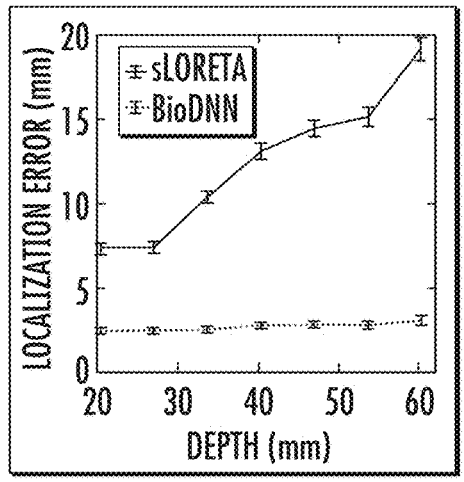
FIGS. 7A-7C show an average localization error of the present invention (BioDNN) versus prior state of the art (sLORETA) implementations.
Figure 7B:
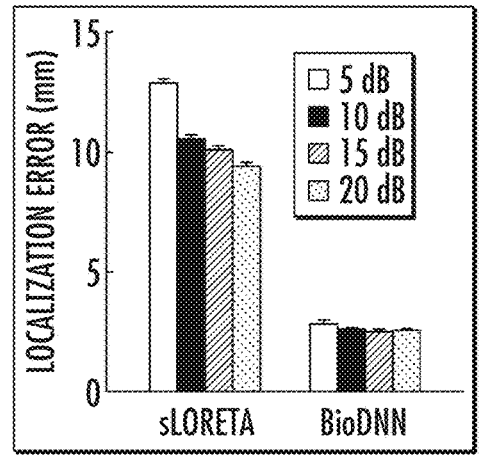
Figure 7C:
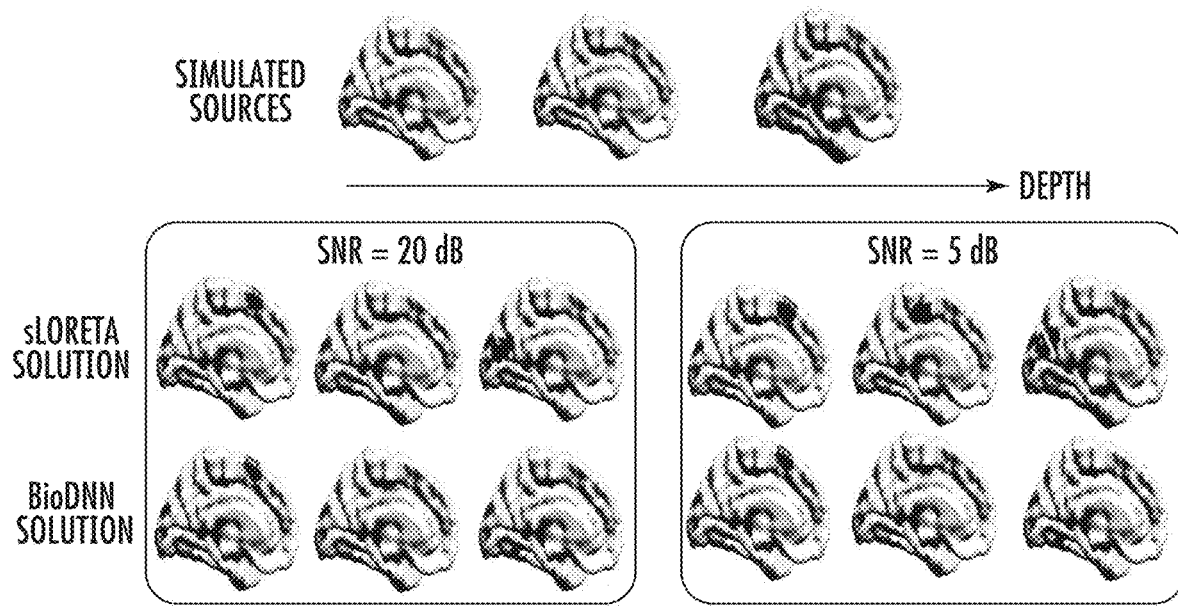

The brain signals were then projected onto the scalp using the lead-field matrix (64 EEG channels) and white Gaussian noise of different variance was added to the scalp potential to obtain signal-to-noise ratios (SNRs) of 5, 10, 15 or 20 dB. In total, 400,000 training examples were generated with different source distributions and noise levels. In the test dataset, 16,000 test examples were generated following the same procedure with one-, two-, three-, and four-patch simultaneously-active sources. The performance of the network was evaluated using the localization error (LE), defined as the distance between the center of the reconstruction to the center of the simulated source patches. The LE for the one-patch configuration is 1.8±3.8 mm. Additionally, the correlation between the simulated and estimated time-course of activity was calculated to be 0.98±0.03. The BioDNN results were initially compared to a benchmark algorithm, namely sLORETA (standardized low-resolution brain electromagnetic tomography) which returned the LE of 4.6±7.4 mm and the correlation of 0.81±0.06. The BioDNN model was then tested for multi-patch source configurations for 2-4 sources. Referring to FIGS. 7A-7C, the BioDNN approach of the present invention demonstrated superior performance in estimating various sources. regardless of the SNR, and depth of the sources, in comparison to the benchmark algorithm (sLORETA). FIG. 7A shows the average localization error of BioDNN and sLORETA as a function of the simulated depth of the sources, and, in FIG. 7B, as a function of noise level. The bars indicate the standard error of mean values. FIG. 7C shows examples of BioDNN and sLORETA solutions wherein green areas indicate simulated and bright-colored areas indicate estimated). Note the superior performance of BioDNN results.

Figure 8A:
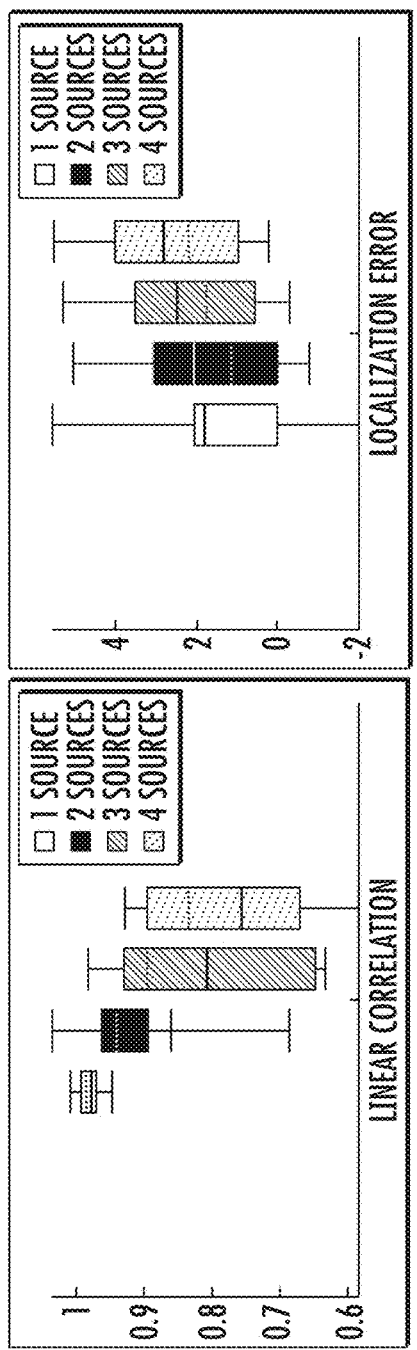
FIGS. 8A-8B show example results for imaging multiple sources using the present invention.
Figure 8B:
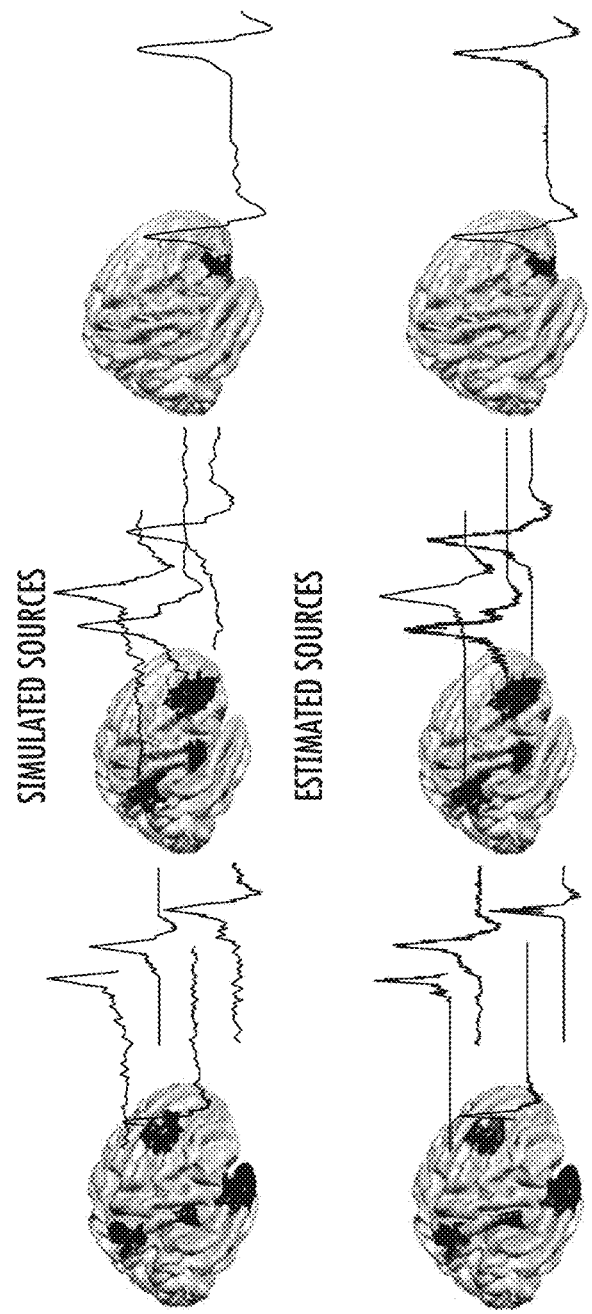

The overall LE of BioDNN obtained for these configurations were 2.1±2.9 mm, 2.5±2.8 mm, and 2.8±2.6 mm, respectively with corresponding time-course correlations of 0.86±0.18, 0.81±0.17, and 0.76±0.17 for one, three, and four-patch source configurations, as depicted in FIG. 8A (averaged over results using SNR of 5, 10, 15, and 20 dB), which shows average linear correlation and localization error between estimated and simulated sources. Examples of BioDNN estimates (source imaging results) can be observed in FIG. 8B for one, three and four-patch source configurations. Note that the BioDNN model performed well on 3 or 4-patch sources even though the deep neural network was only trained on synthetic data from 2-source configurations, which indicates the robustness and generalizability of the present invention. The BioDNN performance was further examined in a 2-source configuration when inter-source distances varied. The exemplary BioDNN results indicate robust performance regardless of source distances, indicating its capability to distinguish multiple closely located sources.

To investigate the efficacy of BioDNN in estimating underlying source extent, the estimated extent of the sources is plotted as a function of the simulated extent for BioDNN results (FIG. 9A). A significant Pearson's correlation of 0.85 was achieved. The precision and recall for the estimated extents were also calculated to be 0.85±0.22 and 0.96±0.11, 0.75±0.22 and 0.82±0.21, 0.70±0.20 and 0.74±0.20, 0.66±0.19 and 0.67±0.19 in one to four-patch simulation cases is shown in FIG. 9B. FIG. 9C graphically illustrates examples of simulated and estimated sources. These results indicate that the BioDNN approach can estimate the location and temporal dynamics of underlying sources, as well as the extent (size) of underlying sources which is important for estimating the extent of brain activation in both healthy subjects and patients with pathology, such as epileptogenic zone in focal epilepsy patients.

Training Dataset and Neural Mass Models—

To train deep neural networks, a large amount of training data is required. It is estimated that, for a one-layer RNN with 500 hidden units, to have a generalization error smaller than 0.1, the training data size needs to be on the order of $O(10^6)$ for a 1 second input at 500 Hz sampling rate. Training the neural network to learn the ESI problem for interictal spikes translates to 11 days of continuous EEG recording with an average spike rate of 1 spike per second. Considering these difficulties for simultaneous intracranial EEG and EEG (or MEG) recordings, collecting a dataset of this size is not feasible. This illustrates the novelty of the present invention. That is, employing a realistic source model to generate synthetic datasets of underlying brain source signals and their corresponding scalp EEG/MEG recordings and using the synthetic datasets to train a deep neural network, to enable electromagnetic source imaging based on actual EEG (or MEG) readings. This novelty is especially true when a biophysical source model is used, such as the NMM models, or other models based on neuronal cellular activity and connectivity.

A novel aspect of the invention is to use NFM models consisting of many interconnected NMMs to generate the training dataset needed for training the DNN. NMM is a mesoscopic level model inspired by neurophysiology that models the average electrical activity of principal neurons and interneurons assemblies, without explicit representation of individual cell activities. The temporal behaviors of the model are defined by differential equations and model parameters, such as tissue properties and connectivity, based on the assumption that neural activities are mainly governed by the interaction between excitatory and inhibitory populations. It was successfully applied in generating rhythmic activity and event-related potentials and was further modified to model interictal spikes. NMM has been used to provide insights into the underlying pathophysiological factors behind epileptic activities or the underlying physiological processes in healthy brains.

The temporal dynamic of the brain activity can be generated using interconnected neural populations, each represented by a physiologically relevant model. The Jansen-Rit model, shown in FIGS. 4A-4B, has been shown to be a reasonable model for many brain activities. A single Jansen-Rit model contains three neuron subpopulations: the main cell (i.e., pyramidal cells), as well as excitatory and inhibitory interneurons. The influence from other neural populations is modeled as an excitatory input p(t) that represents the average pulse density of afferent action potentials. The behavior of each subpopulation is modeled using linear functions $h_e(t)$, $h_i(t)$ that describe how presynaptic information is transformed into postsynaptic information, and nonlinear function $S(v)$ that models the change from average membrane potential of the subpopulation to average pulse density (i.e., average firing rate).

The Jansen-Rit model effectively generates signals at the cortex level. These signals must be processed through the forward problem to generate synthetic EEG recordings. Each NMM element, representing a cortical area, follows the dynamics of the Jansen-Rit model. However, many of these NMM elements will be placed on the cortex to create a neural mass field, to model the distributed underlying brain networks.

To train the model, many different signal types were generated using the Jansen-Rit model. For instance, evoked brain activity, interictal epileptic activity and spontaneous activity such as seizure activity. Multiple sources with varying sizes are simulated and the forward problem is solved to generate the scalp signals. One to five regions can be randomly selected as the source regions with one region serving as the drive node where the NMM element in this region will generate a specific waveform (e.g., interictal spikes), while other selected regions will use the default parameters and are only to be driven by the drive node. Connectivity weights from the drive node to the other regions can be increased from the default value so that spiking signals are observed in these regions, driven to spiking by the drive node. The connectivity weights among selected regions can be determined by a parameter sweep with randomly selected segment pairs over the whole cortex. The correct weight value is large enough that the propagated regions can be activated by the origin source region, but small noise perturbations will not be able to change the NMM state. The NMF can provide tens of millions of training data examples that can be used to train the BioDNN model.

The network structure is optimized by determining the optimal number of layers in the spatial filter as well as the RNN hidden layer numbers, memory gate types, activation unit types, etc. This is achieved by simulations where the end goal is to assess the localization error and correlation of estimated solutions to ground truth when different RNN structures are used to determine the most optimal structure for ESI. Note that the temporal filtering stage can be optimized for any given source model that generates brain-like activity. Basically, the NMF can generate many different signals under various dynamical regime/models and the RNN structure used in the BioDNN can be trained and optimized to learn such dynamics. This is an advantage of the modular structure of BioDNN. This end-to-end evaluation is more straightforward and has been shown to give good results in a example implementation.

According to one embodiment of the invention, simulations can be conducted to further introduce training data to improve the imaging results by additional training. These include the effects of geometry uncertainty and sensitivity of the model parameters and to add critical examples for which the model performance is poor to the training data to improve model performance. These tests include conductivity uncertainties, sensor configuration mismatches, or anatomical structure and network variabilities such as missing or inaccurate structural connectivity. 1. Different MRI for lead-field matrix. MRIs from multiple human subjects can be used to generate the lead-field matrix (than the template used in the training data) with the same conductivity value and sensor locations, which will represent further geometry uncertainty in the training data. 2. Shifted sensor locations. The template sensor cap can tilt 5 degrees to a random direction and then the sensors all be projected on the scalp before calculating the lead-field matrix using the template MRI used for the training data. 3. Changing skull conductivity. The brain-to-skull conductivity ratio can be set in a range of 15-30 with a step of 5 when generating the BEM head model for test datasets. 4. Changing structural connectivity. The diffusion tensor imaging data of multiple individual subjects can be used to derive structure connectivity and can be used to generate additional training data. Random modifications of the structural connectivity matrix can be used to quantify the change of performance for varying amounts of perturbations, i.e., proportion of edges redistributed while keeping the nodal degree (of the structural connectivity matrix) the same.

Figure 10A:
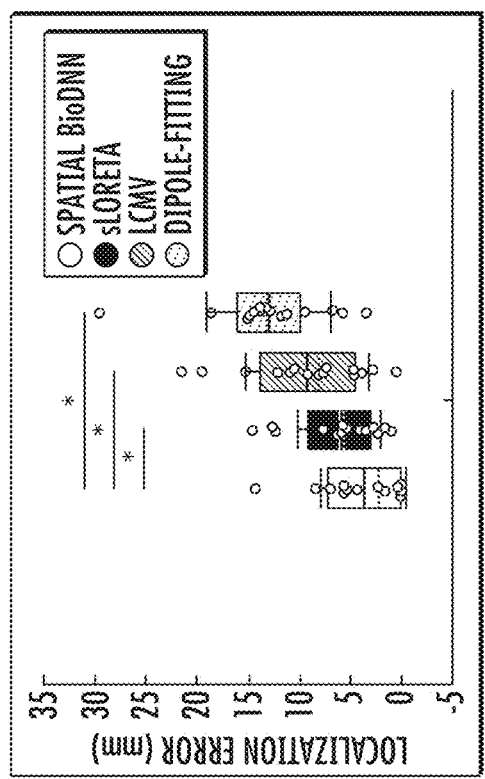
FIGS. 10A-10B show example results for the present invention for imaging and localizing epilepsy sources from EEG recordings, in comparison to other methods.
Figure 10B:
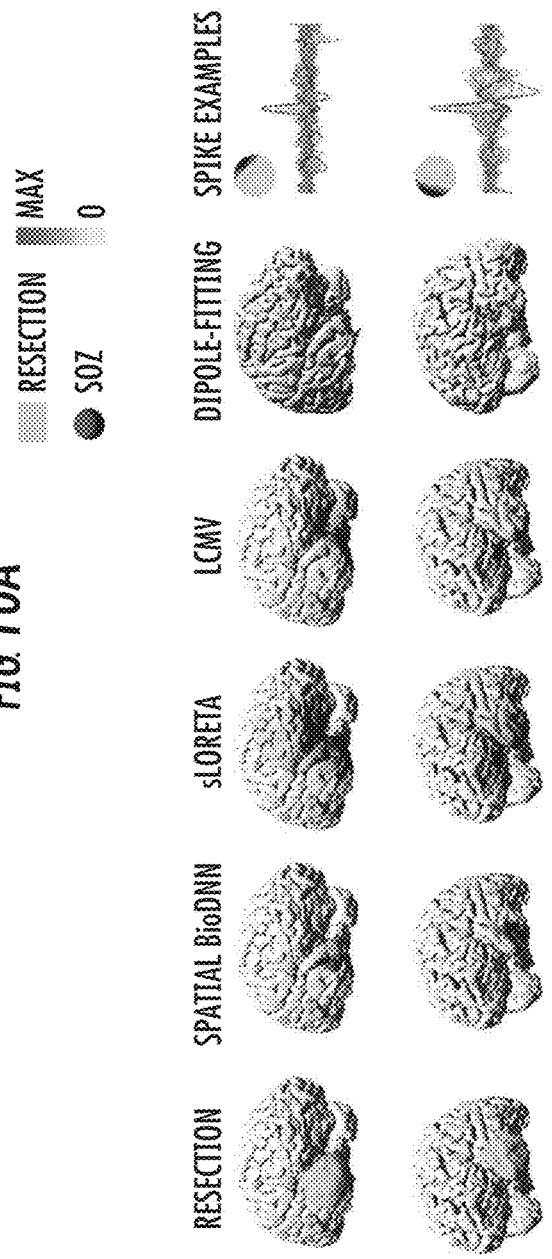

In one example implementation of the invention, a spatial DNN model was used to evaluate the performance of the invention on epilepsy patient data (e.g., the spatial filters of the BioDNN model, as shown in FIG. 5A). The spatial model took an interval of 1-second data around interictal spikes recorded in EEG to spatially determine the region in the brain where spikes are arising from (no estimate of source dynamics). The spatial model was tested in 15 focal epilepsy patients, who underwent surgical resection, to localize the epileptogenic tissue from interictal spikes. All patients suffered from focal epilepsy and did not have observable lesions in the pre-surgical MRI. The localization error (LE), which is defined as the distance between the location of the estimated solution's maximum to the border of the resection region, is used for evaluation. From the presurgical EEG recordings, $N=21\pm22$ interictal spikes were identified for each patient and bandpass filtered between 0.5 and 40 Hz. Each individual spike was localized by the spatial model, as well as three conventional ESI algorithms, namely sLORETA, LCMV (Linearly Constrained Minimum Variance), and dipole-fitting. Paired t-test was used to investigate statistical significance of the obtained results. The LE for the spatial BioDNN model is $3.7\pm4.1$ mm (median 2.3 mm), while for sLORETA, LCMV, and dipole fitting, the LE is $6.1\pm4.1$, $9.2\pm6.0$, $13.0\pm6.0$ mm (median 5.8, 8.1, 13.0 mm), respectively, demonstrating a clear and statistically significant improvement in the spatial BioDNN model. FIGS. 10A-10B illustrate the example results of the spatial BioDNN of the present invention, in comparison to benchmark methods of sLORETA, LCMV, and dipole fitting. FIG. 10A shows the group statistics of the comparison, that the spatial BioDNN of the present invention provided statistically significantly lower localization error than the sLORETA, LCMV, and dipole fitting algorithms. FIG. 10B shows two examples of visualization of source imaging using the spatial BioDNN, sLORETA, LCMV and dipole fitting at interictal spikes of 2 focal epilepsy patients, where the resection area is shown on the most left column. The patients were seizure free after 1 year post-operation follow up.

Figure 11A:
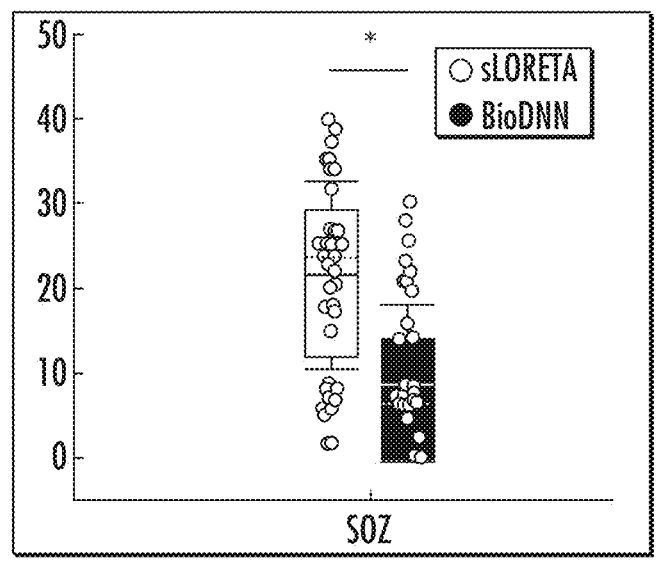
FIGS. 11A-11B show example results for the present invention for imaging epileptic discharges in focal epilepsy patients, in comparison to clinical findings based on intracranial EEG and surgical resection.
Figure 11B:
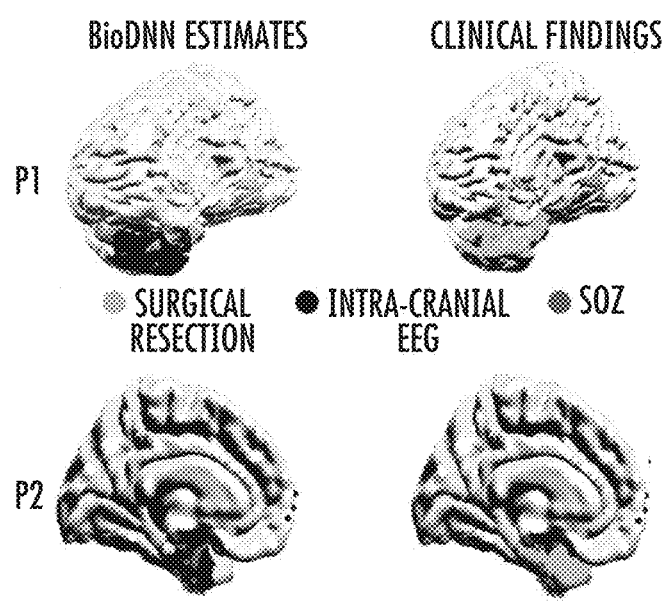

The full spatio-temporal BioDNN model is capable of estimating the location, extent and temporal dynamics of underlying sources responsible for generating scalp EEG, such as interictal spikes. The full BioDNN model was further tested in a group of focal epilepsy patients and the results are shown in FIGS. 11A-11B. FIG. 11A shows the average LE (calculated in 4 epilepsy patients) of $8.8\pm9.2$ mm when comparing to SOZ electrodes, with a median of 6.4 mm while the sLORETA (benchmark algorithm) LE is 23.7±11.0 mm. Examples of estimated interictal sources are also depicted in FIG. 11B, which shows examples of BioDNN ESI results for two patients compared to invasive clinical results. The LE when compared to resection boundary (averaged in 10 patients tested) is 1.5±5.9 mm. These promising testing results indicate that inter-ictal sources from EEG recordings of focal epilepsy patients can be well estimated with the BioDNN approach of the present invention.

Imaging Epileptiform Activities using the BioDNN Approach—

The BioDNN approach of the present invention, due to its modular structure, is flexible in learning different signal types and dynamics. To ensure that the NFM model can generate interictal spikes with various shapes and morphologies, the spikes observed in EEG recordings of a randomly selected subgroup of patients are extracted and these spikes are clustered based on shape and morphology. NFM parameters are spanned to generate different spike types. Once clustered, the generated spikes can include typical observed spike clusters from clinical data. All NFM parameters include all spike clusters in the training data. Once BioDNN is trained with these synthetic spike data, it can be used to image epileptic sources from real spikes recorded in focal epilepsy patients. If the estimated epileptogenic tissue from particular interictal spikes do not match clinical ground truth, the BioDNN structure can be modified for a better match. If a spatial discrepancy between estimates and clinical findings is observed in this random subset, the spatial filter structure can be modified. This will include experimenting with different numbers of layers, activation units and the number of nodes in each layer. By modifying and re-training the network, estimates can be improved. If a temporal discrepancy is observed between estimates and clinical findings, estimated spike shape is different from EEG observed spike shape, the RNN structure can be modified (i.e., temporal filters). Specifically, the number of hidden layers can be increased, which enables the RNNs to model more complex dynamics, and experiment on memory gate unit types. If, incidentally, both spatial and temporal mismatches are observed, the aforementioned operations can be applied simultaneously.

Imaging Seizure Sources from Ictal EEG Recordings Using the BioDNN Approach—

Another example is presented to image spontaneous seizure sources from ictal EEG recordings using the BioDNN approach. The BioDNN was optimized for ictal imaging by varying structural elements in the DNN such as the number of layers in the spatial and temporal modeling units, the number of hidden layers in the RNN structure of the network. A neural field model was employed to generate seizure signals at the brain level adopting a modified Jansen-Rit model proposed and validated previously in the literature. The NMM elements can be connected together to form the NFM that can be used to generate ictal activity. This synthetic seizure simulation data was used to train the BioDNN model.

Figure 12A:
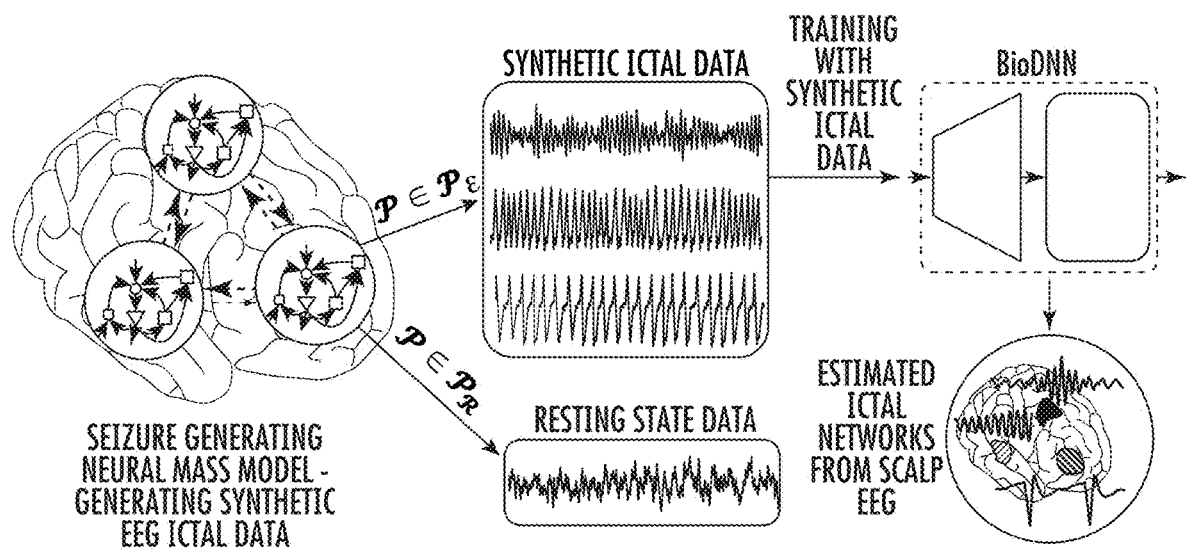
FIGS. 12A-12C show a schematic representation of the neural network of a third embodiment of the present invention using synthesized seizure data, and the use of the present invention for imaging seizure sources from simulated ictal EEG.
Figure 12B:
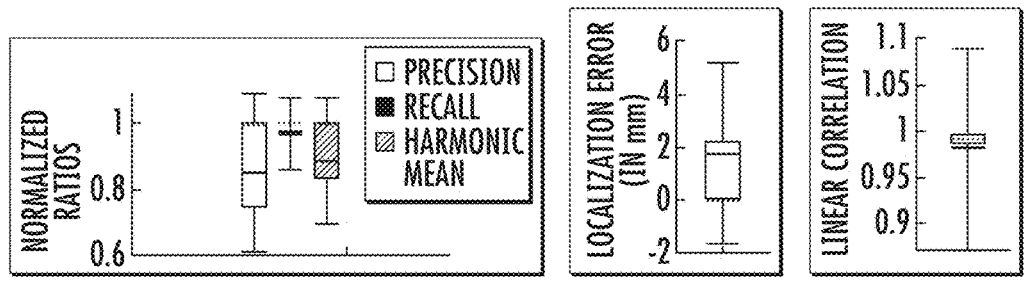
Figure 12C:
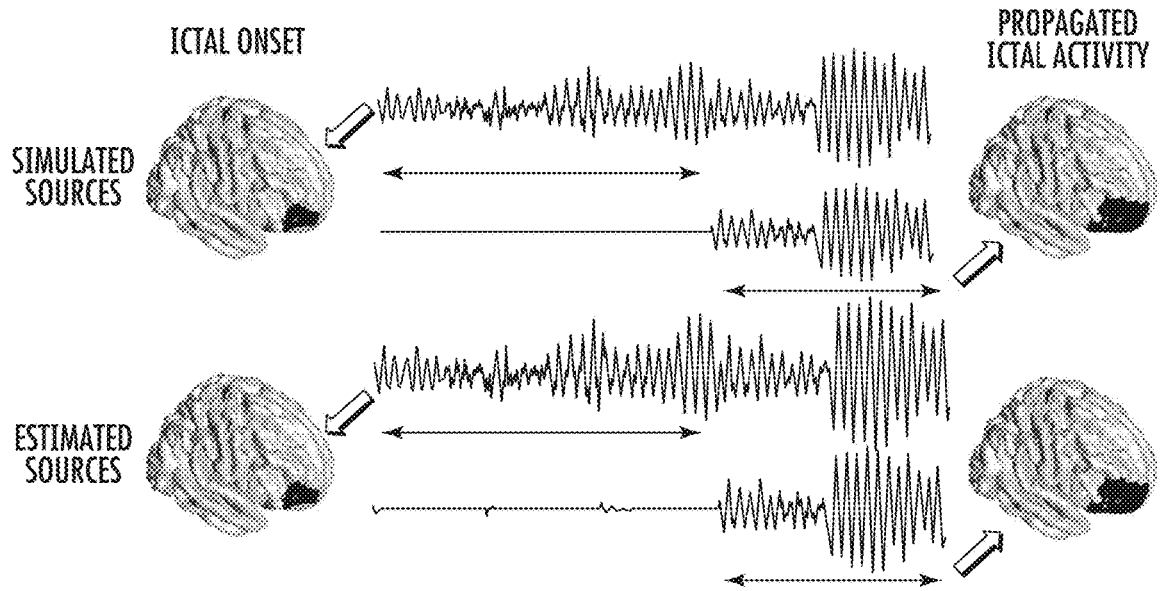
Figure 13A:
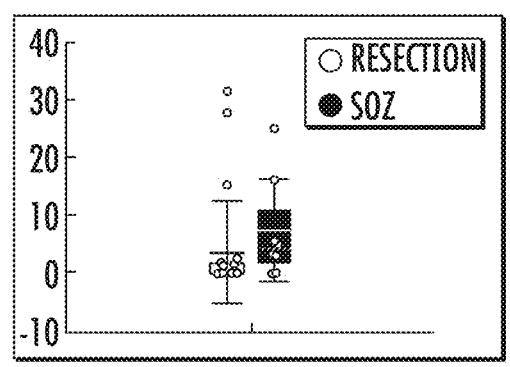
FIGS. 13A-13B show example results for the present invention to image seizure activity from ictal EEG recordings in a group of focal epilepsy patients, in comparison to clinical findings based on intracranial EEG and surgical resection.
Figure 13B:
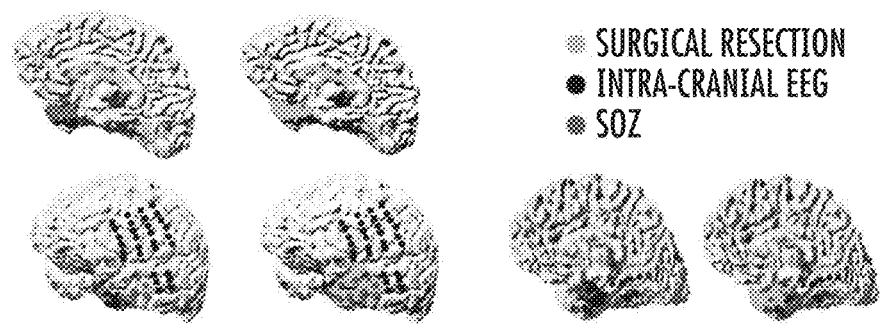

In the example, synthetic ictal data were generated using the NFM which has been shown to be quite effective in generating synthetic ictal signals. This model is capable of generating ictal-like signals once the appropriate parameters are used, as shown in FIG. 12A. The BioDNN model was then trained with these synthetic ictal data and tested in Monte Carlo simulations. The example results indicate the effectiveness of the invention in determining underlying ictal networks. Monte Carlo simulations were performed in which the location and extent of the ictal sources were randomly selected. The performance of the estimated sources was calculated by evaluating the LE, linear correlation of estimated time-courses of activity, precision and recall. The results are presented in FIG. 12B. As it can be seen, average LEs as small as 1.9±3.5 mm and average f-scores (harmonic mean of precision and recall) as high as 0.88±1.9 can be achieved. FIG. 12C illustrates spatial location and temporal evolution of simulated spontaneous seizure activity, as well as estimated seizure activity using the disclosed BioDNN methods. The epileptogenic tissue in the group of focal epilepsy patients who became seizure-free (ILAE 1) after surgical intervention, was analyzed using the BioDNN. The LE is 7.3±8.8 mm (median 4.2 mm) when compared to SOZ, and 3.6±8.8 mm (median 0 mm) when compared to the resection region. The results are summarized in FIGS. 13A-13B which are confirmed by seizure onset zone identified by invasive EEG recordings and/or surgical resection outcome.

While the above example shows applicability of the present invention to image seizure sources from scalp ictal EEG recordings in epilepsy patients, it also illustrates the capability of the present invention to image brain oscillatory activity from scalp EEG (or MEG) recordings that contain signals generated by the oscillatory brain activity, such as those corresponding to specific frequency rhythms including delta rhythm (<4 Hz), theta rhythm (4-7 Hz), alpha rhythm (8-13 Hz), beta rhythm (14-29 Hz), and gamma rhythm (30-80 Hz), or high frequency oscillations (>80 Hz).

Imaging Evoked Brain Activity in Healthy Human.

Another example to image evoked activities in healthy humans by the BioDNN approach will now be presented. Visual evoked potentials (59-channels, then were interpolated into 64 channels to match the input for the neural network) following checkboard stimulation were fed into the trained BioDNN model, which in turn provided source image at latency of 100 ms following stimulation. The BioDNN imaged source is located within visual cortex, as shown in FIG. 14A. Somatosensory evoked potentials (60-channels, then were interpolated into 64 channels) following the little finger stimulation were fed into the trained BioDNN model, which provided source distribution in the primary somatosensory cortex, as shown in FIG. 14B. FIGS. 14A-14B illustrate the capability of the present invention not only to image pathological activity such as epilepsy, but also to image physiological activity in healthy human brains.

Imaging Human Epileptic Activity from MEG Using the BioDNN Approach—

Figure 15:
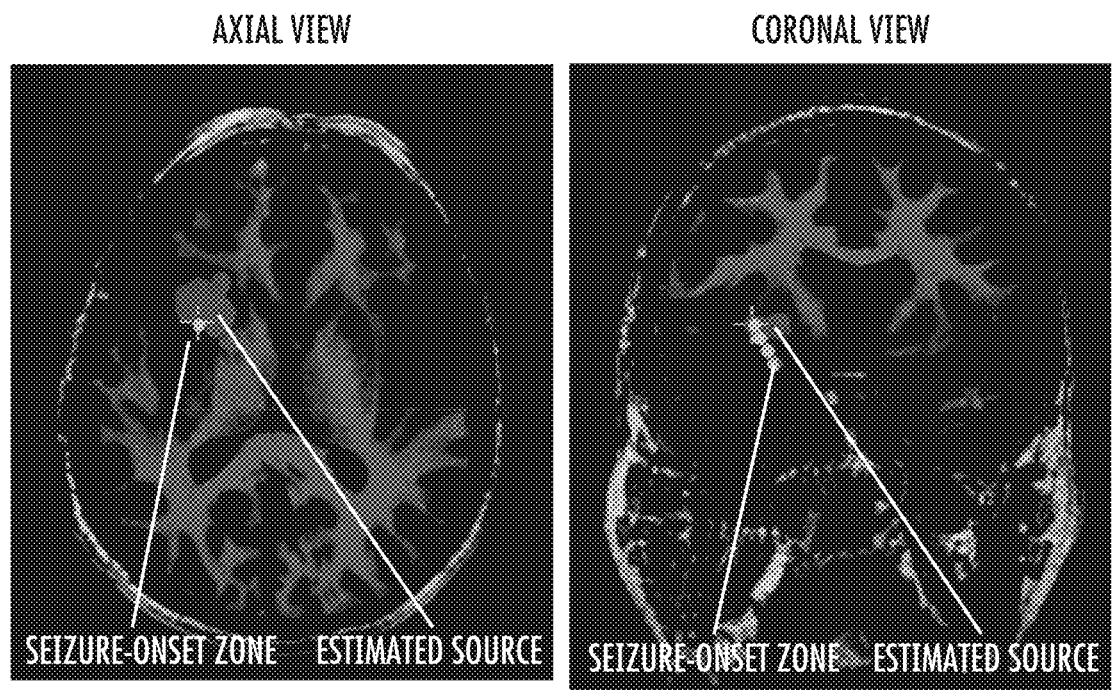
FIG. 15 shows an example result for the present invention to image epileptic sources from interictal spike MEG in a focal epilepsy patient, in comparison to seizure-onset zone identified by intracranial EEG recordings.

In another example application of the present invention, brain activity is imaged using the BioDNN approach from MEG measurements in an epilepsy patient. A deep neural network was trained with synthetic MEG data using NMMs. Scalp MEG recordings during interictal spikes were recorded in a focal epilepsy patient. The BioDNN returned source imaging results from interictal spike MEG that co-localized with seizure onset zone determined by invasive intracranial EEG recordings, as illustrated together with the patient's anatomical MRI images, shown in FIG. 15.

Figure 16:
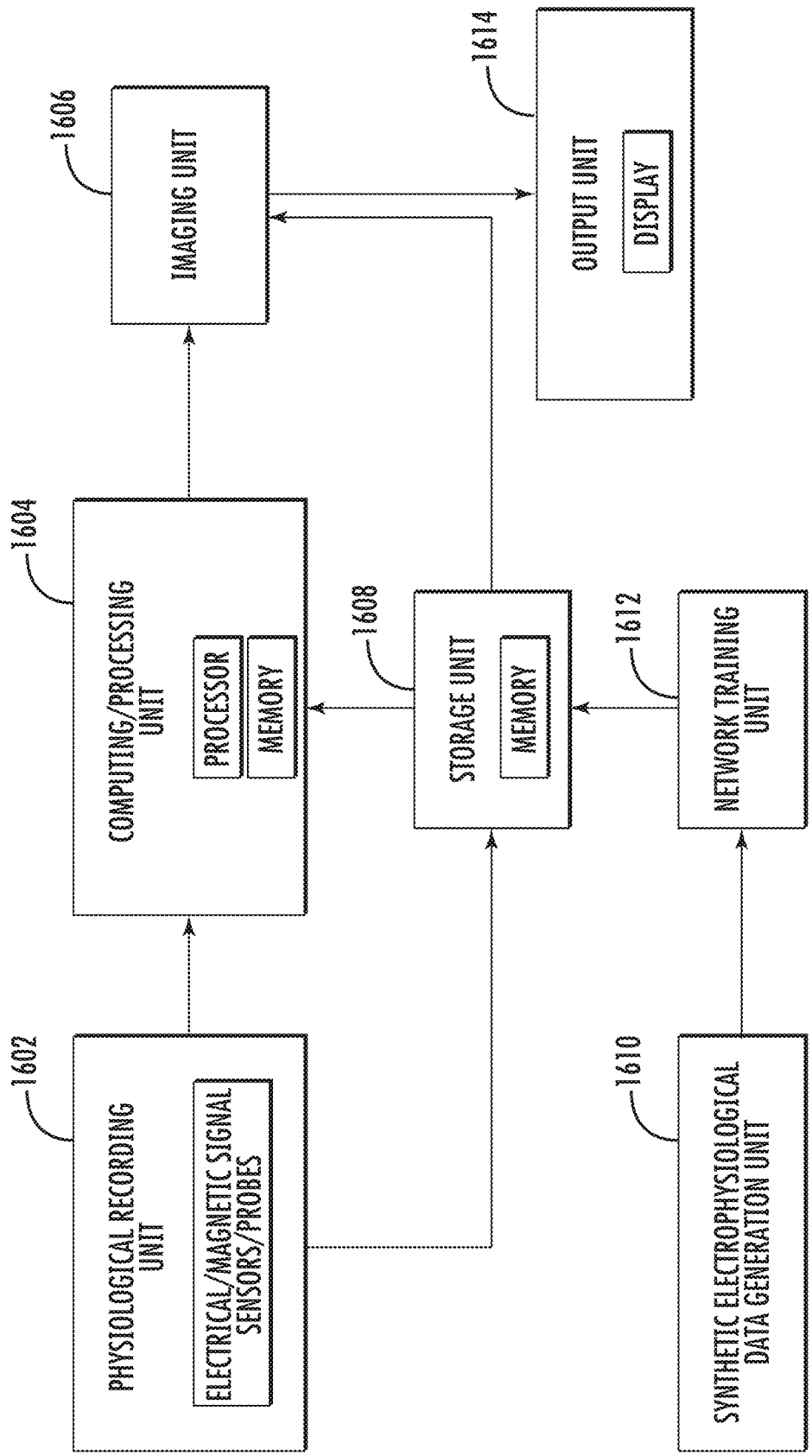
FIG. 16 shows schematic diagrams of a system with the present invention for recording EEG (or MEG), processing recorded signals, training a deep learning neural network using biophysical models, and displaying source imaging results for guiding neuroscience research or clinical applications.

A block diagram of an apparatus implementing one embodiment of the present invention is shown in FIG. 16. A Physiological Recording Unit 1602 is used to collect electric or magnetic signals using a plurality of sensors and records electromagnetic signals at the scalp from sensors of EEG, MEG or a combination of EEG and MEG. The recordings are passed to the Storage Unit for long-term keeping and to be sent to the Computing/Processing Unit for further analysis. The Storage Unit 1608 saves electromagnetic recordings, the deep neural network architecture, weights, and data as well as all processed data in between and at final stages. Synthetic Electrophysiological Data Generation Unit 1610 generates surface EEG (or MEG) data using the neural field model consisting of a number of NMM models and a head volume conductor model. This unit generates synthetic and realistic brain signals, using realistic source models such as, but not limited to, NMM, which will be used to train the deep neural network architecture. The electromagnetic traces and recordings of these signals at scalp, i.e., EEG/MEG, will also be generated for these training datasets. These training data will be passed to the Network Training Unit and will also be saved in memory for further use. The Network Training Unit 1612 trains a deep neural network. The synthetic realistic data generated at the source and projected to the scalp, will be used to train the deep neural network architecture and the weights (and all relevant parameters of the proposed network architecture) are tuned based on these training datasets (and corresponding cross validation schemes, etc.) and saved in the memory to be ultimately passed to the Imaging Unit, where the underlying brain activities are estimated from real EEG/MEG data recordings. Computing/Processing Unit 1604 processes the collected data. This unit performs some pre-processing on the data which includes filtering, removing noisy artefacts, extracting useful features from EEG/MEG recordings to be passed to the Imaging Unit to delineate underlying brain activities from scalp measurements. The Computer Processing Unit 1604 may comprise a processor and a non-transitory, computer-readable storage medium storing instructions that, when executed by the processor, implement the method of the invention. The Imaging Unit 1606 performs source imaging using the trained neural network on collected electrophysiological data. The Imaging Unit 1606 performs the source imaging on the processed/raw EEG/MEG recordings using the trained neural network architecture and weights loaded from the Storage Unit (trained in the Network Training Unit and saved in the Storage Unit), to provide estimates of underlying brain's activity, spatiotemporally. The results are passed to the Output Unit 1614, which displays the final estimates using computer graphics and on realistic brain structures so that physicians or researchers (or users) can better observe and interpret the results. The results are also saved in computer memory.

ESI has been shown to significantly improve the spatial resolution of scalp recorded EEG and MEG. Given the lack of a large amount of EEG or MEG recordings with corresponding source information, synthetic data is needed for deep learning based ESI studies. The present invention addresses this need by disclosing a novel data-driven source imaging framework where realistic brain and EEG/MEG signals are simulated using realistic source models such as biophysically constrained neural mass models for training neural networks, and a deep neural network is trained using the synthetic data. In simulation evaluation and real human subject testing including both EEG and MEG, the disclosed methods demonstrated excellent and consistent results under different signal conditions and proved to be robust when tested and trained on different models.

As stated above, the present invention is applicable to both EEG and MEG source imaging of brain activity. While most descriptions referred to EEG for simplicity of description, the methods disclosed above are applicable to either EEG, or MEG, or combination of EEG/MEG. Furthermore, while the detailed methods were disclosed to image brain sources from scalp EEG or MEG, the present invention is also applicable to image brain activity from recordings made in part or in full within the brain, such as intracranial EEG recordings, or a combination of intracranial EEG and scalp EEG (or MEG) recordings.

While example results are shown for applications to epilepsy source localization and imaging, the present invention may also have applications to study brain normal functions, or to assist in diagnosis and management of other brain disorders. One embodiment can be the application to brain computer interface, where the present invention can be used to efficiently perform ESI from noninvasive EEG or MEG to estimate the intent of a human subject for the purpose of communications or control of an external device or modulating the internal state of the subject for the purpose of rehabilitation or treating brain disorders.

The invention claimed is:

1. A method comprising:
   providing a model of a brain modelling a full brain or a partial area of the brain;
   causing the model to generate synthetic brain source signals;
   determining spatio-temporal estimates of brain electrical sources from electromagnetic measurements in a sensor space; and
   using a trained neural network to provide temporal estimates of sources within the brain based on an input of the spatio-temporal measurements;
   wherein the model of the brain comprises a plurality of interconnected neural mass models.

2. The method of claim 1 wherein the sensor space comprises EEG data or MEG data traces on a scalp.

3. The method of claim 2 wherein the neural network comprises:
   a spatial model that takes into account only spatial information of the EEG or MEG data traces, the spatial information projecting scalp measurements in the simulated sensor data to source space signals in specific source regions in the model of the brain.

4. The method of claim 3 wherein the neural network further comprises:
   a plurality of residual blocks;
   a pooling layer fed by the plurality of residual blocks; and
   a fully connected layer fed by the pooling layer, the fully connected layer having an output size matching the number of source regions.

5. The method of claim 4 wherein each residual block has an input and an output, each residual block comprising:
   two convolutional layers with batch normalization; and
   a ReLU activation function adding the input of the residual block to the output.

6. The method of claim 1 wherein the sensor space comprises electrical data traces inside the head.

7. The method of claim 1 wherein the model of the brain is divided into a number of source regions.

8. The method of claim 7 wherein the source regions are modeled by physical sources including current density distributions.

9. The method of claim 1 wherein the model of the brain comprises a plurality of interconnected biophysical models reflecting neuronal dynamics.

10. The method of claim 1 wherein the model of the brain comprises a plurality of interconnected neural mass models.

11. The method of claim 1 wherein the simulated brain activity models the interaction of neuron sub-populations in the brain using Jansen-Rit models.

12. The method of claim 1 wherein the source signals projected onto the modelled scalp by multiplying the source signals with a lead-field matrix.

13. The method of claim 1 wherein the head volume conductor model is modelled using a boundary element method.

14. The method of claim 13 wherein the boundary element method model is derived from MM images from a human subject.

15. The method of claim 1 wherein the head volume conductor model is modelled using a finite element method.

16. The method of claim 1 wherein the head volume conductor model is modelled using a finite difference method.

17. The method of claim 1 wherein the neural network comprises:
a spatial filter that takes into account spatial information of the simulated sensor data, the spatial information projecting sensor space measurements to source space signals in specific source regions in the model of the brain; and
a temporal filter that takes into account temporal information of the simulated sensor data, the temporal information using current and past values of a time-course of activity from source space signals to estimate activity of the sources at given time in the output unit over a time interval.

18. The method of claim 17 wherein the output of the neural network is a time-course of activity for every source region in the model of the brain.

19. The method of claim 17 wherein the temporal filter comprises a recurrent neural network in which an output of the recurrent neural network is fed back into an input of the recurrent neural network and combined with instantaneous spatial measurements from the spatial filter.

20. The method of claim 17 wherein the spatial filter comprises multiple layers of residual network architecture with each successive layer having increasing dimensions, each layer comprising multiple fully-connected convolutional layers with at least a skip connection and an ELU activation unit.

21. The method of claim 17 wherein the temporal filter comprises multiple hidden layers having long short-term memory as a gate unit with Tanh (tangent hyperbolic) activation units.

22. The method of claim 17 wherein a Jansen-Rit model is used to simulate epileptic interictal spikes, seizure signals, as well as normal brain signals, such as evoked potentials, in the model of the brain for training of the deep neural network.

23. The method of claim 1 wherein the neural network has a number of layers in a range from 3-300 layers.

24. The method of claim 1 wherein the estimated brain electrical activity is used to guide epilepsy surgical planning or neuromodulatory treatment.

25. The method of claim 1 wherein the estimated brain source distributions are used to aid a brain computer interface where ESI signals will be decoded to facilitate communications and device control, or modulating the brain status for rehabilitation, mental health or treating other brain disorders.

* * * * *

UNITED STATES PATENT AND TRADEMARK OFFICE
CERTIFICATE OF CORRECTION

PATENT NO.         : 12,016,634 B2
APPLICATION NO.    : 17/315691
DATED              : June 25, 2024
INVENTOR(S)        : He et al.

Page 1 of 1

It is certified that error appears in the above-identified patent and that said Letters Patent is hereby corrected as shown below:

In the Claims

In Column 17, Claim 14, Line 5, "…MM…" should read "…MRI…"

Signed and Sealed this
Twenty-fourth Day of September, 2024

Katherine Kelly Vidal
*Director of the United States Patent and Trademark Office*